United States Patent [19]

Phillips et al.

[11] Patent Number: 4,543,948
[45] Date of Patent: Oct. 1, 1985

[54] APPARATUS AND METHOD FOR APPLYING ROTATIONAL PRESSURE TO PARTS OF THE BODY

[76] Inventors: Robert L. Phillips; R. Daryl Phillips; Donald C. Mason, all of 2526 12th Ave. South, Great Falls, Mont. 59405

[21] Appl. No.: 516,321

[22] Filed: Jul. 22, 1983

Related U.S. Application Data

[63] Continuation-in-part of Ser. No. 508,897, Jun. 27, 1983, abandoned.

[51] Int. Cl.⁴ .............................................. A61F 3/00
[52] U.S. Cl. ................................................... 128/80 A
[58] Field of Search ............... 128/80 R, 80 A, 80 F, 128/87 R, 87 C, 89 R, 83, 88

[56] References Cited

U.S. PATENT DOCUMENTS

| | | | |
|---|---|---|---|
| 2,815,021 | 12/1957 | Freeman | 128/80 A |
| 3,274,997 | 9/1966 | Hewson, Jr. | 128/87 C |
| 3,730,177 | 5/1973 | Thum | 128/80 A |
| 4,108,168 | 8/1978 | Craig | 128/80 A |

FOREIGN PATENT DOCUMENTS

| | | | |
|---|---|---|---|
| 769463 | 10/1967 | Canada | 128/80 A |
| 229743 | 10/1968 | U.S.S.R. | 128/87 R |

*Primary Examiner*—John D. Yasko
*Attorney, Agent, or Firm*—Mallinckrodt, Mallinckrodt, Russell & Osburn

[57] ABSTRACT

Apparatus for applying rotational pressure to one or more selected parts of the body of a patient includes at least two separate casts placed about portions of the patient's body so as to hold such portions against substantial rotation relative to such casts and interconnections between the separate casts adapted to hold the casts at selected angles of rotation to one another to thereby put rotational pressure on the selected parts of the body. A method for applying rotational pressure to one or more selected parts of the body includes the steps of casting portions of the body, rotating the casts with respect to one another, and locking the casts together in rotated position to thereby place rotational pressure on the selected portion of the body.

13 Claims, 10 Drawing Figures

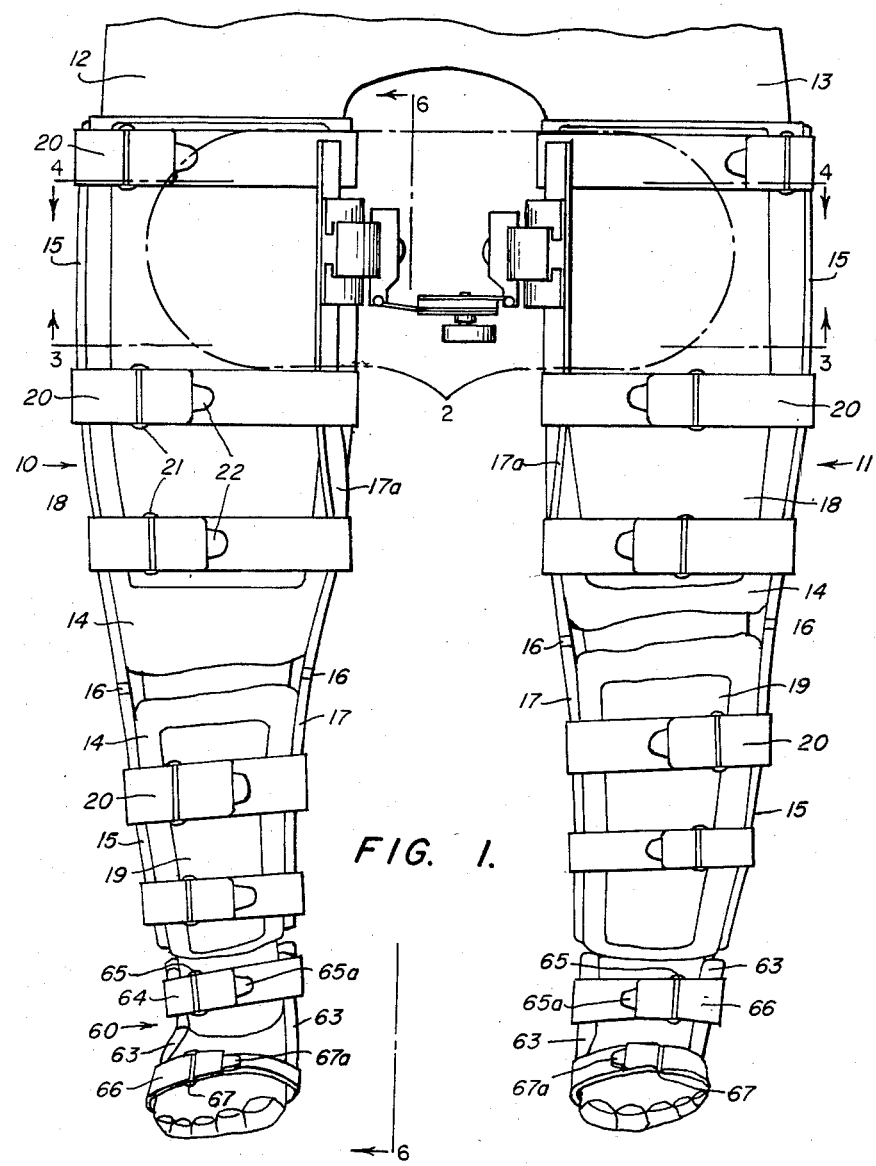
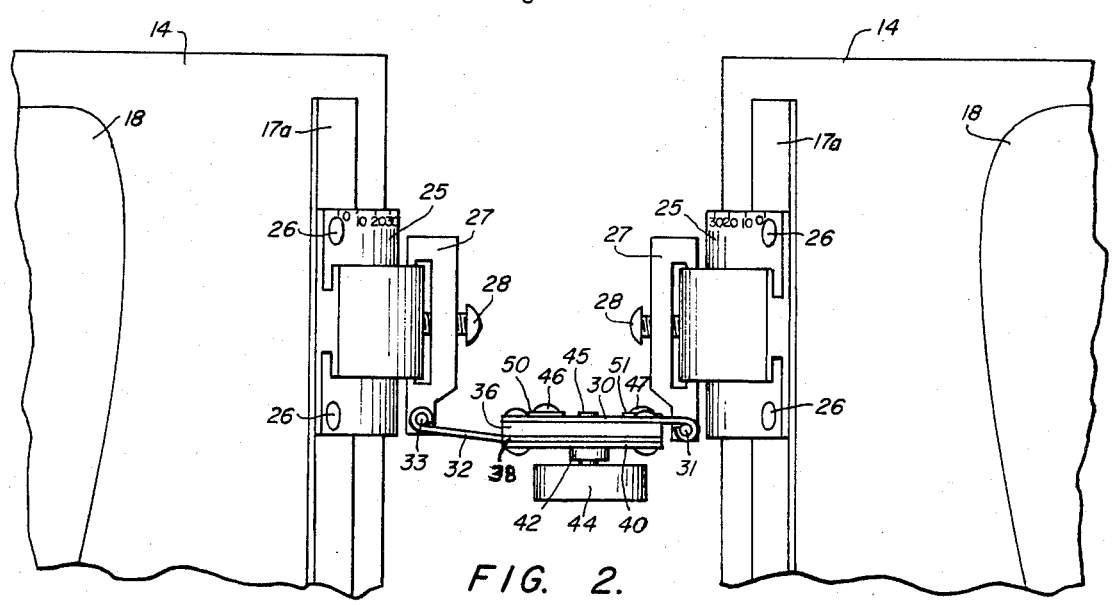
FIG. 1.
FIG. 2.

APPARATUS AND METHOD FOR APPLYING ROTATIONAL PRESSURE TO PARTS OF THE BODY

RELATED APPLICATIONS

This is a continuation-in-part of our copending application Ser. No. 508,897 filed June 27, 1983, now abandoned.

BACKGROUND OF THE INVENTION

1. Field

The invention is in the field of apparatus and methods for applying rotational pressure to various parts of the body and particularly for use in correcting transverse plane deformaties in the hip joints and legs of the human body. Such transverse plane deformaties cause, for example, in-toedness, i.e., pigeon-toedness, or out-toedness.

2. State of the Art

It is currently known that many transverse plane deformaties of the lower limbs are caused by deformaties in the hip joints or deformaties in the tibia, i.e. the lower leg bone. Thus, in-toedness or pigeon-toedness, and out-toedness may be caused by deformaties of the hip joints, deformaties of the tibia, or deformaties in both the hip joints and tibia. It is also generally recognized that these deformaties, at least as caused by the hip joints, may be corrected, or at least partially corrected, by applying corrective pressure to the deformed hip joint while a person is young and the bones are still relatively pliable, usually prior to reaching the age of two years.

The most common apparatus in use today for applying pressure to the hip joints are the Denis Browne Bar and twister cables.

The Denis Browne Bar is a bar with two spaced apart shoes secured thereto. The shoes are rotated for the correction of in-toedness to point the toes outwardly. Thus, a child puts on the shoes on the bar and his feet, legs, and hips are rotated outwardly to put the corrective outward rotational pressure on the hip joints. The Denis Browne Bar is worn by a child while he sleeps.

Twister cables are bars that extend from a belt apparatus worn by a patient down to his shoes and again hold the shoes in a twisted position to twist the feet and legs to apply corrective pressure to the hips.

The problem with the Denis Browne Bar, twister cables, or any similar apparatus and method where rotational force is applied to the foot is that extreme rotational forces must be applied to the foot in order for any rotational force to be applied to the hip joint. This is because when the foot is rotated, rotation is taken up in the midtarsal and subtalar joints of the foot, the ankle, and then the knee, before any rotational pressure is put on the hip joint. Somewhere between twenty and thirty degrees of rotation can be absorbed in the foot before the rotational force extends beyond the foot. These abnormal rotational forces applied to the normal foot, ankle, and knee joints cause problems which may be as bad as the hip joint problems which are being corrected. For example, the rotation outwardly of the feet can cause flat feet, external tibial torsion, and knock knees.

Further, it has been found that where minor cases of in-toedness exist and it appears that the child grows out of the problem, in many cases the child has not really grown out of the problem at all, but merely corrected it by rotating other joints, such as the foot. Thus, in many instances where apparent correction of the problem has taken place, it has been found that the child has compensated by turning the foot, resulting in flat feet.

Attempts have been made to apply rotational pressure directly to the hip joints by means of devices which hold an infants legs so as to apply 90 degree or more flexion and 90 degree abduction to the hip joints (see U.S. Pat. Nos. 2,955,594, 3,114,368, 3,730,177 and 4,108,168). However, such devices are not adjustable over a wide range of hip abduction or flexion and generally are cumbersome with one device requiring the strapping of the child's chest and arms to the device as well as his legs. Further, such devices do not provide for putting rotational pressure on the tibia when the deformity is in the tibia either in addition to a deformity of the hip joint, or apart from the hip joint.

In some cases, the deformities will be in the hip joint, in other cases the deformities will be in the tibia, or in both the hip joint and the tibia. Where deformities are in both, the deformities may not be in the same direction so that it is desirable to put different rotation pressure on the hip and the tibia.

There remains a real need for an apparatus and method to put rotational pressure directly on the hip joints or directly on the tibia, without putting abnormal rotational pressures on other joints. Further, there is a need for such a device that is easy to use and may be used over a wide range of applied rotational pressures.

SUMMARY OF THE INVENTION

According to the invention, apparatus for applying rotational pressure to a selected part of the body of a patient includes at least two separate cast means, each cast means being adapted to be placed about a portion of the patient's body so as to hold that portion against substantial rotation relative to such cast means. Interconnection means interconnect the cast means and are adapted to hold the cast means at an angle of rotation to one another to thereby put rotational pressure on the selected portion of the body.

With the invention, corrective rotational pressure may be applied directly to the hip joints of a human patient by placing a cast means about each leg of the patient and interconnecting such cast means so that the casts are held at an angle of rotation thereby holding the legs at an angle of rotation to put rotational pressure directly on the hip joints of the patient. In this way, rotational pressure may be put on the hip joints with no abnormal rotational pressure put on the feet, ankles, or legs.

The means interconnecting the casts is preferably adjustable so that the casts can be set at varying angles of rotation, and also preferably provides for some relative movement of the casts so that the person wearing the apparatus can move his legs in the frontal and sagittal planes while still maintaining the rotational pressure on the hip joints.

Also with the invention, rotational presure may be applied directly to the tibia of a human patient by placing a cast about the leg of the patient above the ankle to hold the upper end of the tibia and by placing a separate cast about the ankle of the patient to hold the lower end of the tibia. The two casts are interconnected and held at an angle of rotation to put rotational pressure on the tibia.

The invention may be easily constructed so that the casts holding the legs for hip joint pressure also hold the upper end of the tibia for independently putting pressure on the tibia of either or both legs.

THE DRAWINGS

In the accompanying drawings, which illustrate an embodiment of the invention presently contemplated as the best mode of carrying out the invention in actual practice:

FIG. 1 is a front elevation of the lower portion of a human patient showing the cast means for both hip pressure and tibial pressure on the legs of the patient and showing how the interconnection means for hip pressure is positioned;

FIG. 2, an enlarged view of the area enclosed by line 2 in FIG. 1 showing the interconnecting means and a portion of each cast means;

FIG. 3, a horizontal section taken on the line 3—3 of FIG. 1, and drawn to a larger scale;

FIG. 4, a horizontal section taken on the line 4—4 of FIG. 1, and drawn to a larger scale;

FIG. 5, a vertical section taken on the line 5—5 of FIG. 3 but drawn to a larger scale;

FIG. 6, a fragmentary side elevation taken on the line 6—6 of FIG. 1, but drawn to a larger scale;

FIG. 7, a fragmentary vertical section taken on the line 7—7 of FIG. 5;

FIG. 8, a fragmentary rear elevation taken on the line 8—8 in FIG. 6, but drawn to a larger scale;

FIG. 9, a view similar to that of FIG. 8, but showing a different embodiment of the connection of the lower cast to the upper cast; and FIG. 10, a fragmentary side elevation taken on the line 10—10 of FIG. 9 and drawn to a larger scale.

DETAILED DESCRIPTION OF THE ILLUSTRATED EMBODIMENT

Figure 3:
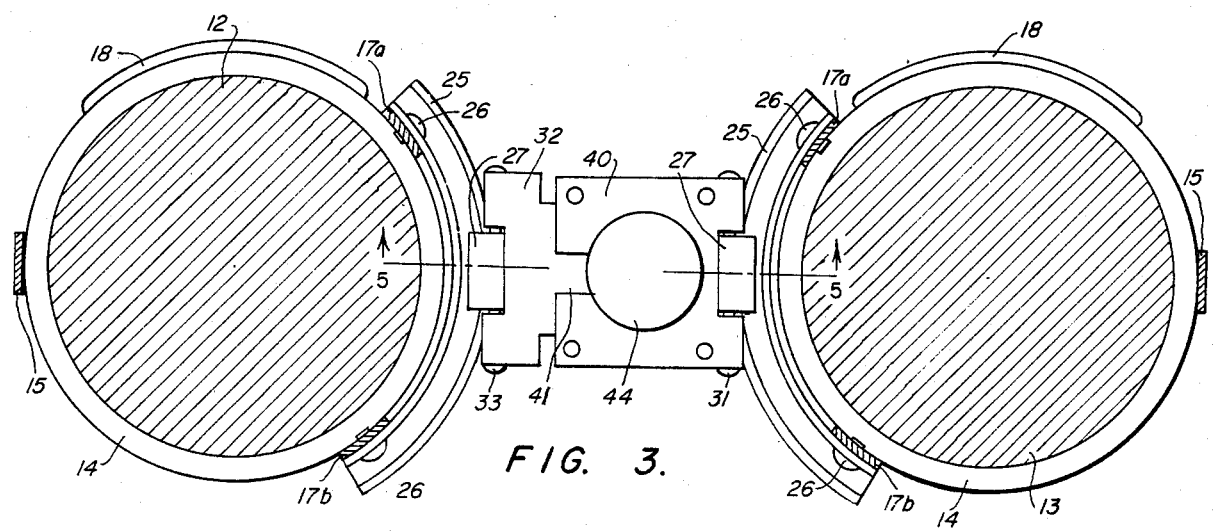

As shown in FIG. 1, an apparatus of the invention for putting rotational pressure on the hip joints of a human includes cast means 10 and 11 for respective legs 12 and 13 of the person using the apparatus. These cast means may vary substantially in construction, the important feature being that the cast means and the leg therein become substantially functionally united in the sense that there is substantially no, or at least very little, relative rotation between the cast and the leg. Thus, when the cast is rotated about its longitudinal axis, the leg is held by the cast and also rotated to substantially the same degree, and held in that rotated position. It will generally be necessary that the cast go over the knee as shown so that it extends about both the upper and lower leg. In some instances, it may be desirable for the cast to also extend about the foot. In the embodiment shown, a separate cast is provided about the ankle and foot for use in putting rotational pressure on the tibia of each leg.

The preferred leg cast for use in the invention is similar to a leg or knee brace such as the Universal Knee Brace manufactured by Medical Designs, Inc., of Arlington, Tex., or that manufactured by Zinco Industries, Inc., of Montrose, Calif. Such braces hold both the upper and lower leg and are hinged at the knee so that the knee can be flexed. This adds to the comfort of the person wearing the brace.

The cast is made up of foam padding 14 which is placed immediately about the legs 12 or 13. Outside brace arms 15 extend longitudinally along the outside of the legs outside of foam padding 14 and also have knee hinges 16 adjacent the knees. The upper portion of inside brace arms 17 are split into two arms 17a and 17b. This is a modification made in the normal brace which has a single arm rather than the split arm.

A femoral plate 18 extends about the front of the leg above the knee while a tibial plate 19 extends about the front of the leg below the knee. Adjustable straps 20 encircle the legs at intervals along the length of the brace to secure all parts together and hold them tightly about the legs. Each strap is made adjustable by passing one end thereof which is provided with Velcro ® material back through a buckle loop 21 secured to the other end of the straps, pulling the strap tight, and securing it in place by means of mating Velcro ® fastening material 22.

The two casts are interconnected by interconnection means which includes tracks 25 secured to and extending between inside brace arms 17a and 17b of each of the casts. Securement of the track to the brace arms may be by rivits 26. A carriage 27 is slidably mounted on each track 25. A screw 28 is provided in each carriage 27. Upon tightening of screw 28, carriage 27 is clamped to the track and locked in place, see FIG. 5.

Figure 4:
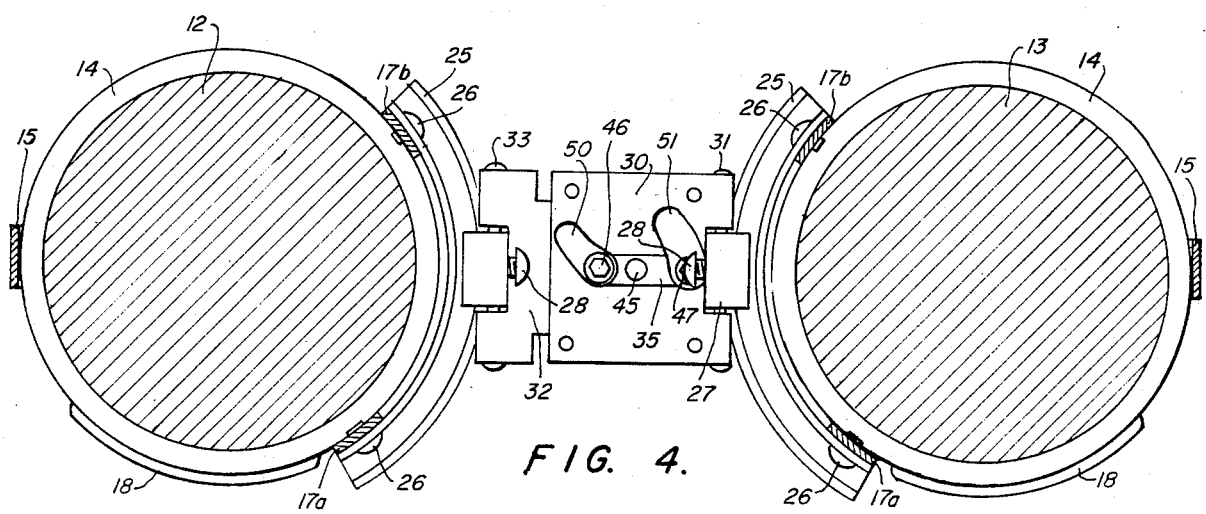
Figure 5:
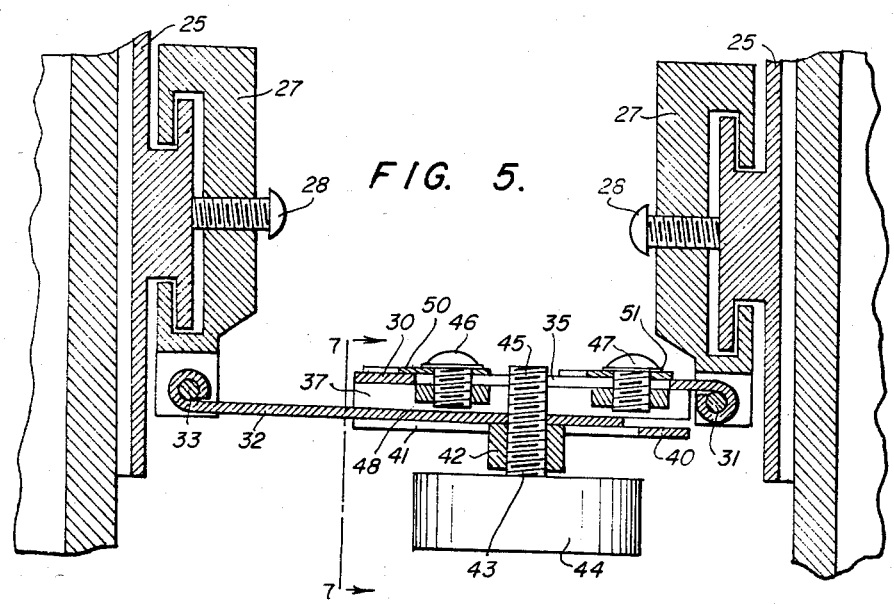
Figure 7:
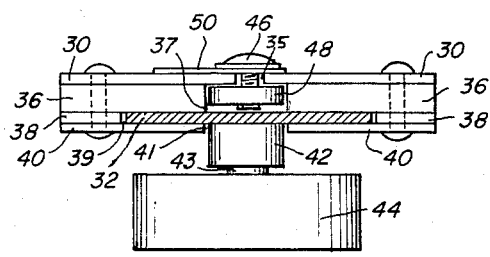

A control plate 30, FIGS. 2 and 5, is hinged to one of the carriages 27 by pin 31 while a control arm 32 is hinged to the other carriage 27 by pin 33. A series of spacer plates are mounted on control plate 30 to form a receiving opening for control arm 32. Thus, control plate 30 has a slot 35 therein, FIGS. 4, 5, and 7. A first spacer 36, FIGS. 2 and 7, is mounted on plate 30 with slot 37 aligned with slot 35. A second spacer 38 is mounted on top of spacer 36 and provides a receiving opening 39 for control arm 32. A bottom plate 40 is mounted on the bottom of spacer 38 and has a slot 41 therein which slidably receives nut 42 secured, such as by welding, to control arm 32.

Screw 43 with large head 44 is threaded through nut 42. With screw 43 loosened so that the bottom portion 45 is below arm 32, arm 32 can be moved into or completely out of receiving opening 39. In this way, the two casts can be completely separated.

For joining the casts, control arm 32 is inserted into receiving pocket 39 and screw 43 tightened through nut 42 so that end portion 45 of screw 43 extends through slot 35 in control plate 30. In such position, arm 32 can slide back and forth with screw 43 moving in slot 35, but the movement is limited by slot 35. With screw 43 in this position, control arm 32 cannot be separated from control plate 30, and the two casts are held together. Screws 46 and 47 are threaded into nuts 48 and 49, respectively, which are held in slot 37. These screw and nut combinations, when loosened, can slide in slot 35 and when tightened, hold their position and act as stops to movement of screw 43 in slot 35 and thus restricts movement of control arm 32 relative to control plate 30. Screws 46 and 47 preferably are provided with a head to accept an Allen wrench rather than a regular screwdriver to make these screws more difficult for the wearer to adjust. It is also preferred that comma shaped washers 50 and 51, FIG. 4, be provided so that if the screws 46 or 47 are adjusted inwardly from the ends of slot 35, the washers can be adjusted to cover the exposed portion of the slot between its end and the screw. With such portion of the slot so covered, a user will not accidentally connect the control mechanism with end 45 of screw 43 extending into the wrong portion of slot 35.

It is preferred that the end portion 45 of screw 43 be unthreaded or otherwise configured so that screw 43 cannot be completely removed from nut 42. This insures that the screw 43 is always with the apparatus and does not get lost.

With the casts secured on the legs, any rotation of the casts will tend to cause rotation of the legs which will put rotational pressure on the hip joints. The apparatus of the invention is intended to be used under the direction of a doctor. Thus, in use, the doctor would initially fit the apparatus to the patient, and adjust it to the patient's requirements. After the casts have been fitted to the patient, the doctor will determine the amount of rotational pressure to be applied to the hip joints and by loosening screws 28 in carriage 27 will rotate the casts the desired amount. To help the doctor in this task, it is preferred that a degree of rotation scale be marked on the tracks 25 as shown in FIG. 2. When the casts have been rotated to the desired positions, the screws 28 are tightened to lock the carriage in position on the tracks and thus, lock the desired cast rotation into the apparatus. The doctor will also determine the amount of movement of the legs to be allowed in the in and out direction and adjust screws 46 and 47 to provide for this movement. As treatment progresses, it is easy for the doctor to adjust the rotational pressure applied as is necessary.

Once set, the patient merely needs to loosen screw 43 by turning head 44 to separate the two casts and then remove them in normal manner by loosening or removing straps 20 of the cast. To put on the apparatus, the casts are put on the legs in normal manner, and then control arm 32 is slid into receiving slot 39 and screw 43 tightened to secure the casts together in proper position. Once the casts are thus secured, the rotational pressure is automatically applied to the legs.

While the described interconnection of the casts provide for easy separation of the casts and for various adjustments, an interconnection menas as described is not necessary. All that is required is an interconnection means that provides for holding the two casts at a desired angle of rotation to one another to thereby apply desired rotational pressure to the hip joints.

In addition to applying rotational pressure to the hip joints of a patient, the apparatus as shown in the drawings may also be used for applying rotational pressure to the tibia, i.e., the lower leg bone. For this purpose, additional casts 60 and 61 are provided at the lower ends of casts 10 and 11 respectively. These additional casts fit about the ankle and foot of each leg. The lower portion of casts 10 and 11, i.e., the part below the knee, secure the upper end of the tibia in the leg in position and tend to hold them against rotation relative to the casts. The lower end of the tibia is secured to the ankle in the body in such a way that there can be no relative rotation between the upper end of the ankle and the tibia. Thus, a cast which holds the ankle against substantial relative rotation therewith, essentially holds the lower end of the tibia from substantial relative rotation therewith. Then, by holding the lower casts 60 and 61 at angles of rotation with the leg casts 10 and 11 respectively, rotational pressure can be put on the tibia.

Figure 6:
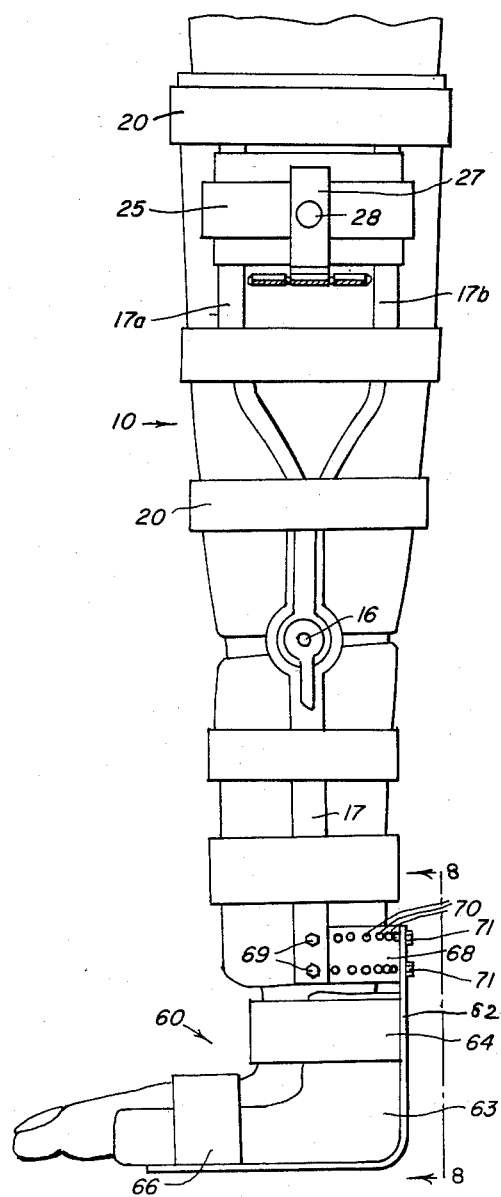
Figure 8:
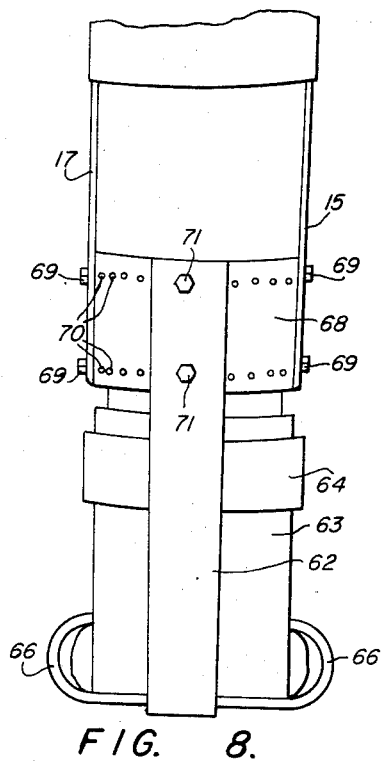
Figure 9:
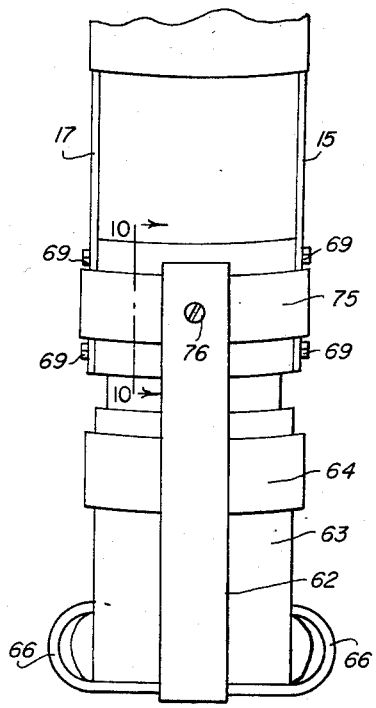

As shown in FIGS. 6, 8, and 9, the lower casts 60 or 61 are made up of a rigid supporting and connecting member 62 which is adapted to extend along the back of the ankle and curve around the heel to extend under the foot. This member may be made of various materials, one preferred material being aluminum. Secured to member 62 is an ankle and foot receiving shell 63 made of soft but substantially shape-retaining material such as a plastic foam. The ankle and foot of the user are comfortably but snugly received in this shell. A flexible strap 64 is secured to supporting member 62 and extends about shell 63 so that shell 63 may be tightened about the sides and back of the ankle. Strap 64 further extends about the front of the ankle to hold it securely in place in shell 63. Strap 64 is preferably constructed similarly to straps 20 with areas of mating Velcro ® so that it may be easily secured about the ankle. Thus, the end of strip 64 which has Velcro ® material attached thereto, is looped through buckle 65 and secured in place with mating Velcro ® 65a, FIG. 1.

A flexible strap 66 is secured to supporting member 62 under the foot and extends about shell 63 to tighten the shell about the foot and to hold the foot securely in place. This strap, one end of which has Velcro ® secured thereto, is passed through buckle 67 and secured in place with mating Velcro ® 67a. Of course, various other arrangements of buckles of various types could be used to connect the ends of straps 64 and 66 to provide for securement and adjustment.

Supporting member 62 is adapted to be secured to the lower end of leg cast 10 or 11 in a manner that allows the two connected casts to be held at an adjustable angle of relative rotation. For this purpose, an attachment plate 68 is secured to brace arms 15 and 17 at the lower end of the leg cast, such as by bolts 69, and extends around the back of the cast as shown, FIGS. 6, 8, and 9. A series of holes 70 are provided in two equally vertically spaced rows along the attachment plate 68. Two holes are provided in the top portion of support and connecting member 62 of lower cast 60, the holes adapted to mate with a hole in each of the upper and lower row of holes 70 in attachment plate 68. The support member is bolted in place by bolts 71 which securely attaches the lower ankle and foot cast to the lower end of the leg cast. The amount of relative rotation that is locked in between the two casts is determined by which holes in the attachment plate 68 are aligned with the holes of support member 62 when bolts 71 are inserted. It will be seen from the drawings that the two casts can be secured together, i.e., interconnected, over a wide range of relative rotations of the two casts.

Figure 10:
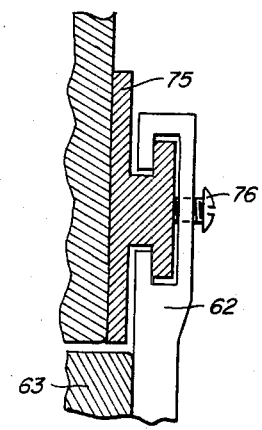

If it is desired to make the relative rotation of the two casts continuously adjustable, a track 75, FIGS. 9 and 10, similar to track 25, may be used as attachment plate 68 with the top of support and connecting member 62 being configured to fit about and slide on track 75. A screw 76 is provided so that when the leg and ankle casts are moved to the desired angle of relative rotation, screw 76 is tightened and the two casts are held securely in that position.

Where it is desired to apply rotational pressure only to the hips of a patient, only the two leg csts are necessary. There is no need to include the lower ankle casts. Where it is only desired to apply rotational pressure to the tibia, only a leg and ankle cast are needed. In such instances, there is no need for any interconnection between leg casts, and if only one tibia needs treatment, there is no need for casts on the leg with the tibia not needing treatment.

While the casts have been described with reference to a particular structure, the casts could take many forms, such as conventional plaster or hexalite casts, or various other brace designs. The important thing is that there be little or no substantial relative rotational movement between the cast and the part of the body within the cast.

Further, while the invention has been specifically described in relation to creating corrective rotational pressure on the hip joints and the tibia, it could be used with appropriate changes in the casts for the body parts involved, on various other parts of the body.

While it has been generally recognized that hip joint deformities may be corrected by applying corrective measures up to the age of about two years, it has been found that correction using the present invention is possible in much older children, even up to the age of about eight.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. Apparatus for applying rotational pressure to the hip joints of a human patient, comprising two separate cast means, each being adapted to be placed about a leg of a patient so as to hold such leg against substantial rotation relative to such cast means; and means adjustably and directly, without contacting or being secured to other body parts, interconnecting the separate cast means adapted to hold the cast means at an adjustable angle of rotation along their longitudinal axises one to another to cause rotation of each leg to thereby put rotational pressure on each hip joint.

2. Apparatus for applying rotational pressure to the hip joints of a human patient, comprising two separate cast means, each being adapted to be placed about a leg of a patient so as to hold such leg against substantial rotation relative to such cast means; and means interconnecting the separate cast means adapted to hold the cast means at angles of rotation to one another to thereby put rotational pressure on each hip joint, such interconnecting means including track means secured to at least one of the cast means and extending in a plane perpendicular to the longitudinal axis of the cast means and mating means adapted to be rigidly secured to said track means at points along said track means, securement at different points providing different degrees of rotation of the casts along their longitudinal axises one to another.

3. Apparatus for applying rotational pressure to the hip joints of a human patient according to claim 2, wherein a track and associated mating means is provided for each cast means.

4. Apparatus for applying rotational pressure to the hip joints of a human patient according to claim 2, wherein the interconnecting means includes means for allowing the cast means to move in relation to one another while still maintaining the same angle of rotation between the casts.

5. Apparatus for applying rotational pressure to the hip joints of a human patient according to claim 3, wherein the interconnecting means includes means connecting the two associated mating means.

6. Apparatus for applying rotational pressure to the hip joints of a human patient according to claim 5, wherein the means connecting the two associated mating means is hingedly secured to each mating means to allow some relative movement of the cast means one to another along their longitudinal axises while still maintaining the same angle of rotation between the casts.

7. Apparatus for applying rotational pressure to the hip joints of a human patient according to claim 6, wherein the means connecting the two associated mating means allows a predetermined amount of movement of the cast means away from or toward one another to thereby allow the patient some spreading movement of the legs while still maintaining the same angle of rotation between the casts.

8. Apparatus for applying rotational pressure to the hip joints of a human patient according to claim 7, wherein the predetermined amount of travel of the casts toward or away from one another is adjustable.

9. Apparatus for applying rotational pressure to the hip joints of a human patient according to claim 8, wherein the means connecting the two associated mating means is constructed in at least two separable parts so that the two casts can be separated to thereby facilitate application and removal of the casts to and from the legs.

10. Apparatus for applying rotational pressure to the tibia of a human patient comprising two separate cast means, one being adapted to be placed about a portion of the leg of the patient above the ankle so as to hold the upper portion of the tibia against substantial rotation relative to such cast means and the other adapted to be placed about the ankle of the patient so as to hold the ankle and the lower portion of the tibia against substantial rotation relative to such cast means; an attachment plate secured to one cast having a plurality of attachment means; and a connecting means on the other cast adapted to mate with selected attachment means on the attachment plate, the particular attachment means selected determining the amount of relative rotation between the casts thereby determining the rotational pressure on the tibia.

11. Apparatus for applying rotational pressure to the tibia of a human patient according to claim 10, wherein the attachment means on the attachment plate are holes adapted to have bolts therethrough, and the connecting means has holes adapted to mate with selected holes of the attachment plate and, wherein bolts pass through the mated holes to secure the connection means and the attachment plate.

12. A method for applying rotational pressure to selected parts of a body of a patient according to claim 2, wherein the selected part of the body is the tibia in a leg of a human, wherein the step of placing cast means comprises the step of placing a cast means on the leg of the patient above the ankle of the selected leg to which tibia pressure is to be applied to hold the upper end of the tibia against substantial rotation with respect to the cast means; placing a cast means about the ankle of the same leg to hold the lower end of the tibia against substantial rotation with respect to the cast means; wherein the rotating step comprises rotating one cast in relation to the other cast; and wherein the locking step comprises locking the two cast means together in rotated position so that rotational pressure is applied to the tibia.

13. Apparatus for applying rotational pressure to the tibia of a human patient comprising two separate cast means, one being adapted to be placed about a portion of the leg of the patient above the ankle so as to hold the upper portion of the tibia against substantial rotation relative to such cast means and the other adapted to be placed about the ankle of the patient so as to hold the ankle and the lower portion of the tibia against substantial rotation relative to such cast means; track means secured to one cast means; and mating means attached to the other cast means and adapted to be rigidly secured to said track means at points along said track means, securement at different points along the track providing different degrees of relative rotation between the casts thereby determining the rotational pressure on the tibia.

* * * * *